United States Patent
Lange et al.

(10) Patent No.: US 10,668,004 B2
(45) Date of Patent: Jun. 2, 2020

(54) AGENT AND METHOD FOR THE TEMPORARY DEFORMATION OF KERATINOUS FIBERS

(71) Applicant: Henkel AG & Co. KGaA, Duesseldorf (DE)

(72) Inventors: Julia Bibiane Lange, Bad Bramstedt (DE); Rene Scheffler, Ellerau (DE); Diane Metten, Hamburg (DE); Cyrielle Martinez, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 77 days.

(21) Appl. No.: 15/844,653

(22) Filed: Dec. 18, 2017

(65) Prior Publication Data

US 2018/0168990 A1     Jun. 21, 2018

(30) Foreign Application Priority Data

Dec. 19, 2016 (DE) .................. 10 2016 225 472

(51) Int. Cl.
*A61Q 5/06* (2006.01)
*A61K 8/81* (2006.01)

(52) U.S. Cl.
CPC .......... *A61K 8/8152* (2013.01); *A61K 8/8176* (2013.01); *A61K 8/8182* (2013.01); *A61Q 5/06* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 9,511,008 B2 * | 12/2016 | Hoffmann | ............... A61K 8/37 |
| 2011/0135589 A1 | 6/2011 | Knappe | |
| 2015/0335566 A1 | 11/2015 | Knappe et al. | |
| 2017/0135945 A1 | 5/2017 | Knappe et al. | |

FOREIGN PATENT DOCUMENTS

| | | | |
|---|---|---|---|
| DE | 102013226806 A1 | 6/2015 | |
| DE | 102015204148 A1 * | 9/2016 | ............... A61Q 5/06 |
| WO | 2016142013 A1 | 9/2016 | |

OTHER PUBLICATIONS

Intellectual Property Office, Search Report under Section 17(5) for United Kingdom Patent Application No. GB1721110.3 dated Jul. 10, 2018.

* cited by examiner

*Primary Examiner* — Jyothsna A Venkat
(74) *Attorney, Agent, or Firm* — Lorenz & Kopf, LLP

(57) ABSTRACT

The present disclosure relates to a cosmetic preparation for temporary deformation of hair, which contains a combination of two specific copolymers. The cosmetic preparation provides an extremely good hold.

2 Claims, No Drawings

AGENT AND METHOD FOR THE TEMPORARY DEFORMATION OF KERATINOUS FIBERS

CROSS-REFERENCE TO RELATED APPLICATION

This application claims priority to German Patent Application No. 10 2016 225 472.3, filed Dec. 19, 2016, which is incorporated herein by reference in its entirety.

TECHNICAL FIELD

The present disclosure relates to a cosmetic preparation for hair fixing or for temporarily deforming keratinous fibers, in particular human hair, wherein the composition contains a combination of two specific copolymers.

BACKGROUND

The temporary design of hairstyles for a longer period of time of up to several days normally employs the use of firming active ingredients. Therefore, hair treatment agents that temporarily shape the hair play a role. Corresponding agents for temporary deformation normally contain synthetic polymers and/or waxes as a firming active ingredient. Agents aiding the temporary deformation of keratinous fibers can be packaged, for instance, as hairspray, hair wax, hair gel or mousse.

One feature of an agent for temporary deformation of hair, also referred to hereinafter as a styling agent, includes giving the treated fibers in the newly modeled shape—i.e. a shape impressed on the hair—the strongest possible hold. This is also referred to as a strong hairstyle hold or a high degree of hold of the styling agent. The hairstyle hold is essentially determined by the type and amount of firming active ingredients used, wherein the other components of the styling agent can also have an influence.

In addition to a high degree of hold, the styling agent must fulfill a series of additional requirements. They can be roughly divided in to characteristics on the hair, characteristics of the respective formulation, e.g. characteristics of the foam, gel or sprayed aerosol, and characteristics relating to the handling of the styling agent. This includes, in for example, moisture resistance, low stickiness (tack) and a balanced conditioning effect. Furthermore, a styling agent may be universally applicable for all hair types, insofar as possible, and mild to the hair and skin.

In order to satisfy some features, a multitude of synthetic polymers was developed as firming active ingredients, which can be used in styling agents. The polymers can be divided into cationic, anionic, nonionic and amphoteric firming polymers. For example, the polymers may create a polymer film when used on the hair, which lends the hairstyle a strong hold and is sufficiently flexible in order to not break under stress. If the polymer film is too brittle, so-called flakes form, i.e. residue, which detach during movement of the hair and give the impression that the user of the corresponding styling agent has dandruff. Similar problems arise when waxes are used as a firming active ingredient in the styling agent. If the styling agent is a gel or a paste, the polymers nay also have thickening properties.

Cationic polymers that are used in hair fixing products are copolymers with two or more structural units. Specific copolymers of this type, based on the monomers N-vinylimidazole and N-vinyllactam with the INCI designations POLYQUATERNIUM-44, POLYQUATERNIUM-46 and POLYQUATERNIUM-68 and their use in agents for temporary hair deformation are described in the German application DE 10 2013 226 806 A1. Such copolymers are available under the trade names Luviquat® UltraCare, Luviquat® Hold and Luviquat® Supreme.

Additional anionic polymers that are used in hair fixing products are crosslinked anionic amphiphilic polymers that contain a (meth)acrylic acid unit and a (meth)acrylic acid oxyalkylene alkyl ester unit. Such polymers are described in the international patent application WO 2016/142013 A1 and are commercially available, for example, under the name BALANCE® RTF (INCI: acrylates/ceteareth-20 methacrylate crosspolymer). In styling products, this polymer essentially has the task of a thickening agent and film former.

The present disclosure addresses the problem of providing additional polymer combinations, which is exemplified by good film-forming and/or fixing properties, has a very high degree of hold without the need to dispense with flexibility and good moisture resistance—such as sweat and water resistance— and is also suitable for production of stable viscous and stable transparent cosmetic preparations. For example, currently available styling agents can be improved, because a good combination of stiffness and long-term hold (high humidity curl retention) is not always sufficiently available. Therefore, the present disclosure addresses the problem of preparing such styling agents that provide the aforementioned properties, for example with regard to good stiffness and a good, long-term hold.

BRIEF SUMMARY

As contemplated herein, this was achieved by employing a combination of two specific anionic copolymers.

The present application provides:
1. A cosmetic preparation for temporary deformation of keratinous fibers, which contains:
a) at least one copolymer (a), which includes at least one of the following structural units:
(a1) at least one monomer selected from the quaternated N-vinylimidazoles,
(a2) at least one monomer selected from the quaternated N-vinyllactams, and
b) at least one crosslinked acrylate copolymer (b) differing from the copolymer (a), which includes at least one of the following structural units (B-I) and (B-II):

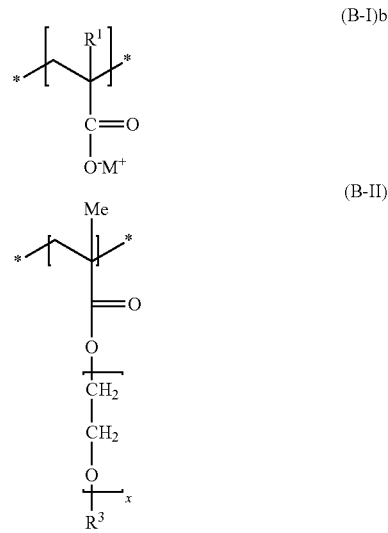

wherein
$R^1$ denotes a hydrogen atom or a methyl group,
$R^3$ denotes a $(C_8-C_{30})$-alkyl group,
$M^+$ denotes a physiologically tolerated cation and
x denotes an integer from about 5 to about 35.

2. Cosmetic preparation according to point 1, wherein the copolymer (a) includes at least one of the following structural units:
(a1) 3-methyl-1-vinylimidazolium methyl sulfate,
(a2) at least one monomer selected from N-vinylcaprolactam and N-vinylpyrrolidone, preferably N-vinylpyrrolidone
(a3) N-vinylimidazole and
(a4) at least one monomer selected from acrylic acid amide and methacrylic acid amide, preferably methacrylic acid amide.
3. Cosmetic agent according to one of the points above, exemplified in that the percent by weight of copolymer (b) of the total weight of the cosmetic agent is from about 0.1 to about 10 wt. %, such as from about 0.5 to about 8.0 wt. % and for example from about 1.0 to about 7.0 wt. %.
4. Cosmetic agent according to one of the points above, wherein the copolymer (a) has the INCI designation POLYQUATERNIUM-68, particularly Luviquat® Supreme (BASF).
5. Cosmetic preparation according to one of the points above, wherein the radical $R^1$ in the structural unit (B-I) denotes a methyl group.
6. Cosmetic preparation according to one of the points above, wherein $R^3$ R in the structural unit (B-II) of the crosslinked acrylate copolymer (b) denotes a $(C_{12}-C_{20})$-alkyl group, such as a $(C_{14}-C_{20})$-alkyl group and for example a $(C_{16}-C_{18})$-alkyl group.
7. Cosmetic preparation according to one of the points above, wherein the x in the structural unit (B-II) of the crosslinked acrylate copolymer (b) denotes an integer from about 10 to about 24, such as from about 16 to about 22, for example about 20.
8. Cosmetic preparation according to one of the points above, wherein $R^3$ in the structural unit (B-II) of the crosslinked acrylate copolymer (b) denotes a combination of linear $C_{16}$- and $C_{18}$-alkyl groups.
9. Cosmetic preparation according to one of the points above, wherein the preparation contains the anionic copolymer (b) in a proportion of from about 0.1 to about 10 wt. %, such as from about 0.5 to about 7.0 wt. %, for example from about 1.0 to about 5.0 wt. %, relative to the total weight of the cosmetic preparation.
10. Cosmetic preparation according to one of the points above, wherein the anionic acrylate copolymer (b) is a crosspolymer with the INCI designation acrylates/ceteareth-20 methacrylate crosspolymer, such as BALANCE® RCF (AkzoNobel).
11. Cosmetic preparation according to one of the points above, wherein the anionic copolymer is (a) Luviquat Supreme (BASF) and the anionic copolymer is (b) BALANCE® RCF (AkzoNobel).
12. Cosmetic preparation according to one of the points above, which, relative to the total weight of the cosmetic preparation, contains:
from about 0.1 to about 10 wt. % of the anionic copolymer (a), and
from about 0.1 to about 10 wt. % of the anionic copolymer (b).
13. Cosmetic preparation according to one of the points above, containing, relative to the total weight of the cosmetic preparation,
from about 0.5 to about 8.0 wt. % of the anionic copolymer (a), and
from about 0.5 to about 7.0 wt. % of the anionic copolymer (b).
14. Cosmetic preparation according to one of the points above, wherein the weight ratio of polymers a) and b) in the cosmetic preparation is from about 5:1 to about 1:5, such as from about 3:1 to about 1:3 and for example from about 2:1 to about 1:2.
15. Cosmetic preparation according to one of the points above, wherein the preparation additionally contains at least one copolymer (c) which is different from the copolymers (a) and (b), such as an anionic or nonionic polymer (c).
16. Cosmetic preparation according to one of the points above, exemplified in that it additionally contains, relative to its total weight,
c) polyvinylpyrrolidone and/or vinylpyrrolidone/vinyl acetate copolymer, such as polyvinylpyrrolidone.
17. Cosmetic preparation according to point 15, exemplified in that the proportion by weight of the polyvinylpyrrolidone and/or vinylpyrrolidone/vinyl acetate copolymer c) is from about 1.0 to about 10 wt. % of the total weight of the cosmetic preparation, such as from about 2.0 to about 8.5 wt. % and for example from about 3.0 to about 7.0 wt. %.
18. Cosmetic preparation according to one of the points above, wherein the preparation contains water and the proportion by weight of the water of the cosmetic preparation is between about 50 and about 95 wt. %, such as between about 60 and about 90 wt. % and for example between about 65 and about 85 wt. %.
19. Cosmetic preparation according to one of the points above, wherein the preparation is provided as hair gel, hairspray, mousse or hair wax.
20. Use of a cosmetic preparation according to one of points 1 to 19 for the temporary deformation of keratinous fibers.
21. Use of a cosmetic preparation according to one of points 1 to 19 for improvement of the hold of temporarily deformed keratinous fibers.
22. Use of a cosmetic preparation according to one of points 1 to 19 for improvement of the moisture resistance of temporarily deformed keratinous fibers.
23. Method for the temporary deformation of keratinous fibers, such as human hair, wherein the cosmetic preparation according to one of the items 1 to 19 is applied to keratinous fibers.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Surprisingly, it was discovered in the context of the present disclosure that a combination of two known components that are already used in styling products can achieve an improved hold of styling products. Other conventionally required properties of styling products, such as moisture resistance, stiffness and low stickiness are retained in the process. Such a good combination of properties was not to be expected even when the individual components are known and was surprising. Experiments showed that the combination of the two components produced a strong overadditive, in other words a synergistic effect with regard to the hold, which is manifested in the 3PB test (3-Point Bending test) and in the HHRC-Test (High Humidity Curl Retention test).

As contemplated herein, the term keratinous fibers comprises fur, wool and feathers, for example human hair.

The essential components of the inventive cosmetic preparation are the cationic copolymer (a) and the crosslinked copolymer (b) differing from copolymer (a).

The cosmetic preparation of the present disclosure contains the cationic copolymer (a) and crosslinked acrylate copolymer (b) in conventional and suitable quantities the styling agent, which can be adjusted for the special application and packaging.

The disclosed preparation can contain the copolymer (a), for example, in a quantity of from about 0.1 to about 10 wt. % relative to the total weight of the disclosed preparation. Proportions of the copolymer (a) from about 0.5 to about 8.0 wt. % and for example from about 1.0 to about 7.0 wt. % are useful, specified as the solids content of active substance in the cosmetic preparation.

This inventive cosmetic preparation contained the crosslinked acrylate copolymer (b) in a quantity from about 0.1 to about 10 wt. %, such as from about 0.5 to about 7.0 wt. %, for example from about 1.0 to about 5.0 wt. % relative to the total weight of the cosmetic preparation, specified as the solids content of active substance in the cosmetic preparation.

The agents contain a cationic copolymer (a) as a first component, which includes at least two structural units of formulae (a1) and (a2). Additional structural units can also be present.

Some preparations are exemplified in that they contain at least one copolymer (a), which
(a1) contains at least one structural unit according to the formula (A-I) wherein
R denotes a $C_1$- bis $C_{30}$-alkyl group, a $C_1$- to $C_4$-aralkyl group, a $C_2$- bis $C_6$-alkenyl group or a $C_2$ to $C_6$-hydroxyalkyl group and
$X^-$ denotes a physiologically tolerated anion
(a2) and contains at least one additional structural unit according to formula (A-II), wherein n denotes 1, 2 or 3 as the number of methylene units.

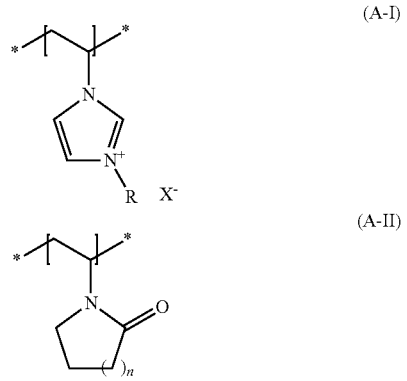

Copolymers (a) can also have additional structural units that are polymerized by employing adding appropriate monomers during the polymerization process.

In formula (A-I),
R denotes a $C_1$- bis $C_{30}$-alkyl group, a $C_1$- to $C_4$-aralkyl group, a $C_2$- bis $C_6$-alkenyl group or a $C_2$ to $C_6$-hydroxyalkyl group. Examples of preferred groups R are —$CH_3$; —$CH_2CH_3$, —$CH_2CH_2CH_3$, $CH(CH_3)_2$, —$(CH_2)_3CH_3$, —$CH_2$—$CH(CH_3)_2$, $CH(CH_3)CH_2CH_3$, —$C(CH_3)_3$, —$CH_2OH$, —$CH_2CH_2OH$, —$CH_2CH_2CH_2OH$, —$CH(OH)CH_2CH_3$, —$CH_2CH(OH)CH_3$.

$X^-$ denotes a physiologically tolerable anion, and exemplary anions are chloride, bromide, iodide, sulfate, methosulfate, ethylsulfate, tosylate and tetrafluoroborate.

Some embodiments have agents exemplified in that the monomer (A-I) is a salt of 3-alkyl-1-vinylimidazolium with physiologically tolerable anions, such as 3-methyl-1-vinylimidazolium methyl sulfate.

In formula (A-II), n denotes the number of methyl groups. When n=about 1, formula (A-II) denotes a vinylpyrrolidone unit, when n=about 2 it denotes a vinylpiperidinone unit and when n=about 3 it denotes a vinylcaprolactam unit. Some agents are exemplified in that monomer (A-II) is selected from N-vinylcaprolactam and N-vinylpyrrolidone. N-vinylpyrrolidone is suitable for use as monomer (A-II).

Some agents are exemplified in that they contain at least one copolymer (aI) as copolymer (a), which
contains at least one structural unit according to formula (A-I), wherein R denotes a methyl group and X denotes methosulfate,
contains at least one additional structural unit according to formula (A-II), wherein n denotes 1 methylene unit.

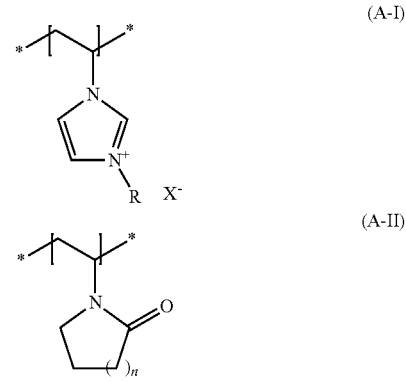

Some copolymers (a1) contain from about 10 to about 30 mol. %, such as from about 15 to about 25 mol. % and for example about 20 mol. % of structural units according to formula (A-I) and from about 70 to about 90 mol. %, such as from about 75 to about 85 mol. % and for example about 80 mol. % structural units according to formula (A-II).

In this context, the copolymers (a1) may contain, in addition to polymer units resulting from the integration of the indicated structural units according to formula (A-I) and (A-II) into the copolymer, a maximum of about 5 wt. %, preferably a maximum of about 1 wt. % of polymer units, which go back to the integration of other monomers. The copolymers (a1) may include structural units of formula (A-I) and (A-II) and can be described by the general formula

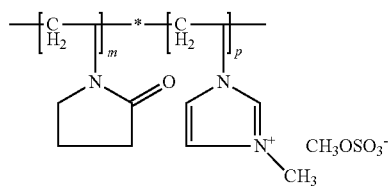

wherein indexes m and n each vary according to molar mass of the polymer and may not mean that they are block polymers. Moreover, structural units of formula (A-I) and formula (A-II) can be distributed statically in the molecule.

Such N-methylvinylimidazole/vinylpyrrolidone copolymers are designated as POLYQUATERNIUM-44 according to INCI nomenclature and are commercially available, for example, from BASF under the trade name Luviquat® UltraCare.

Some agents contain a copolymer (aI), which has molar masses within a specific range. In this context, examples include hair deformation agents with which the copolymer (aI) has a molar mass of from about 50 to about 400 kDa, such as from about 100 to about 300 kDa, for example from about 150 to about 250 kDa and from about 190 to about 210 kDa.

In addition to the copolymer(s) (aI) or its or their position, the agents I can also contain copolymers (aII) having additional structural units of formula (A-II), wherein n denotes the number 3.

Other agents are exemplified in that they contain at least one copolymer (aII) as copolymer (a), which
  contains at least one structural unit according to formula (A-I), wherein R denotes a methyl group and X denotes methosulfate,
  contains at least one additional structural unit according to formula (A-II), wherein n denotes about 1 methylene unit,
  contains at least one additional structural unit according to formula (A-II), wherein n denotes about 3 methylene units.

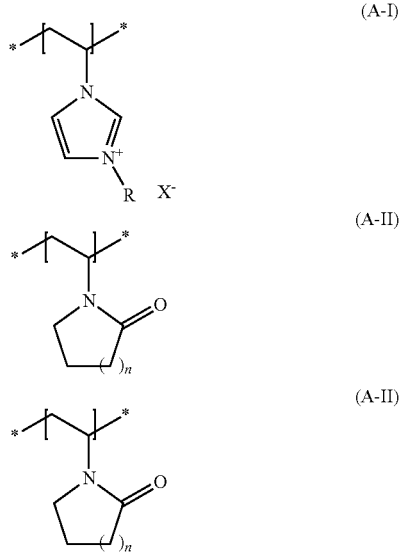

In this context, the copolymers (aII) may contain, in addition to polymer units resulting from the integration of the indicated structural units according to formula (A-I) and (A-II) into the copolymer, a maximum of about 5 wt. %, preferably a maximum of about 1 wt. % of polymer units, which go back to the integration of other monomers. The copolymers (aII) include structural units of formula (A-I) and (A-II) and can be described by the general formula

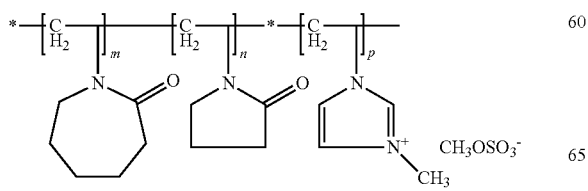

wherein indexes m, n and p each vary according to molar mass of the polymer and may not mean that they are block polymers. Moreover, structural units of formula (A-I) and formula (A-II) can be distributed statically in the molecule.

Such N/-methylvinylimidazole/vinylpyrrolidone/vinylcaprolactam copolymers are designated as POLYQUATERNIUM-46 according to INCI nomenclature and are commercially available, for example, from BASF under the trade name Luviquat® Hold.

Some copolymers (aII) contain from about 1 to about 20 mol. %, such as from about 5 to about 15 mol. % and for example about 10 mol. % structural units according to formula (A-I) and from about 30 to about 50 mol. %, such as from about 35 to about 45 mol. % and for example about 40 mol. % structural units according to the formula (A-II), where n=about 1 and from about 40 to about 60 mol. %, such as from about 45 to about 55 mol. % and for example about 60 mol. % structural units according to formula (A-II), where n=about 3.

Some agents contain a copolymer (aII), which has molar masses within a specific range. In this context, examples include hair deformation agents with which the copolymer (b2) has a molar mass of from about 100 to about 1000 kDa, such as from about 250 to about 900 kDa, for example from about 500 to about 850 kDa and from about 650 to about 710 kDa.

In addition to the copolymer(s) (aI) and/or (aII) or in its or their place, the agents can also contain copolymers (aIII) which have, as additional structural unit, structural units of formula (A-II), where n denotes the number 3, as well as additional distructural units from the group of vinylimidazole units and additional structural units from the group of acrylamide and/or methacrylamide units.

Some agents are exemplified in that the copolymer (aIII) of at least the following structural units:
(a1) at least one monomer selected from quatemated N-vinylimidazoles,
(a2) at least one monomer selected from N-vinyllactams,
(a3) the monomer N-vinylimidazole and
(a4) at least one monomer selected from acrylic acid amide, methacrylic acid amide, N-alkyl acrylic acid amide and N-alkyl methacrylic acid amide.

Some agents are exemplified in that they contain at least one copolymer (aIII) as copolymer (a), which
  contains at least one structural unit according to formula (A-I), wherein R denotes a methyl group and X denotes methosulfate,
  contains at least one additional structural unit according to formula (A-II), wherein n denotes about 1 methylene unit,
  contains at least one additional structural unit according to formula (A-III)
  contains at least one additional structural unit according to formula (A-IV)

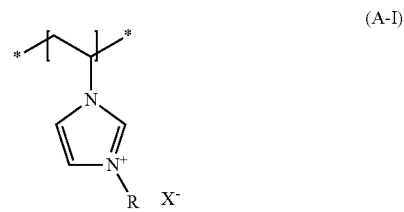

-continued

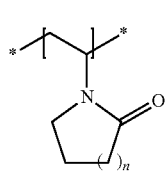
(A-II)

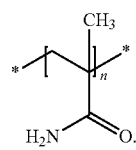
(A-III)

(A-IV)

In this context, the copolymers (aIII) may contain, in addition to polymer units resulting from the integration of the indicated structural units according to formula (A-I), (A-II), (A-III) and (A-IV) into the copolymer, a maximum of about 5 wt. %, such as a maximum of about 1 wt. % of polymer units, which go back to the integration of other monomers. The copolymers (aIII) may include structural units of formula (A-I), (A-II), (A-III) and (A-IV) and can be described by the general formula

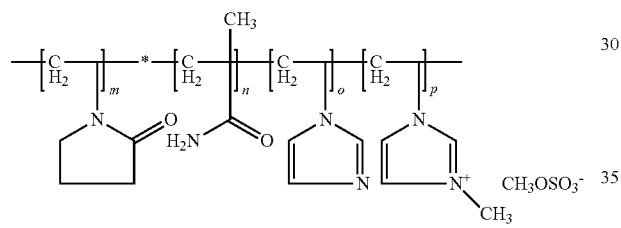

wherein indexes m, n, o and p each vary according to molar mass of the polymer and may not mean that they are block polymers. Moreover, structural units of formulae (A-I), (A-II), (A-III) and (A-IV) can be distributed statically in the molecule.

Some agents are exemplified in that the copolymer (a) includes at least the following structural units:
3-methyl-1-vinylimidazolium methyl sulfate,
at least one monomer selected from N-vinylcaprolactam and N-vinylpyrrolidone,
N-vinylimidazole and
at least one monomer selected from acrylic acid amide and methacrylic acid amide.

Consideration is given to inventive agents in which the copolymer (a) includes at least the following structural units:
3-methyl-1-vinylimidazolium methyl sulfate,
N-vinylpyrrolidone,
N-vinylimidazole and
methacrylic acid amide.

In regard to the cosmetic properties of the inventive agents, it has been found to be beneficial if the copolymer (a) includes at least about 70 wt. %, such as at least about 80 wt. %, more preferably about 90 wt. % and for example about 95 wt. % of the structural units 3-methyl-1-vinylimidazolium methyl sulfate, N-vinylpyrrolidone, N-vinylpyrrolidone, and methacrylic acid amide.

Such N-methylvinylimidazole/vinylpyrrolidone/vinylcaprolactam/methacrylic amide copolymers are designated as POLYQUATERNIUM-68 according to INCI nomenclature and are commercially available, for example, from BASF under the trade name Luviquat® Supreme.

Some copolymers (aIII) contain from about 1 to about 12 mol. %, such as from about 3 to about 9 mol. % and for example about 6 mol. % structural units according to formula (A=i) and from about 45 to about 65 mol. %, such as from about 50 to about 60 mol. % and for example about 55 mol. % structural units according to formula (A-II), where n=about 1 and from about 1 to about 20 mol. %, such as from about 5 to about 15 mol. % and for example about 10 mol. % structural units according to formula (A-III) and from about 20 to about 40 mol. %, such as from about 25 to about 35 mol. % and for example about 29 mol. % structural units according to formula (A-IV).

Some agents contain a copolymer (aIII), which has molar masses within a specific range. In this context, consideration is given to hair deformation agents with which the copolymer (b3) has a molar mass of from about 100 to about 500 kDa, such as from about 150 to about 400 kDa, for example from about 250 to about 350 kDa and from about 290 to about 310 kDa.

One cosmetic preparation for temporary deformation of keratinous fibers contains:
(a) at least one copolymer (a), which includes at least one of the following structural units:
(a1) at least one monomer selected from the quaternated N-vinylimidazoles,
(a2) at least one monomer selected from the quaternated N-vinyllactams
and
(b) at least one crosslinked acrylate copolymer (b) differing from the copolymer (a), which includes at least one of the following structural units (B-I) and (B-II):

(B-I)

(B-II)

wherein
$R^1$ denotes a hydrogen atom or a methyl group,
$R^3$ denotes a $(C_8\text{-}C_{30})$-alkyl group,
$M^+$ denotes a physiologically tolerated cation and
x denotes an integer from about 5 to about 35
The crosslinked anionic acrylate copolymer (b) includes at least the following structural units (B-I) and (B-II).

The crosslinked acrylate copolymer (b) is amphiphile based on the integral structural units. A person skilled in the art understands "amphiphile" to generally mean that one and the same molecule comprises hydrophilic structural elements (e.g. of formula (B-I)) and lipophilic structural elements (e.g. of formula (B-II)).

In the above formulae and all formulae below, a chemical bond bearing the symbol * denotes a free valence of the corresponding structural fragment. Ammonium ion and cationic organic compounds having a quaternized nitrogen atom are suitable as physiologically compatible cations $M^+$ for compensation of the negative charge of the amphiphilic, anionic polymer metal cations of the physiologically compatible metals from the groups Ia, Ib, IIa, IIb, IIIb, VIa or VIII of the period system of elements. Cationic organic compounds having a quaternized nitrogen atom are, for example, produced by employing protonation of primary, secondary or tertiary organic amines with an acid, or by employing permanent quaternization of said organic amines. Examples of such cationic organic ammonium compounds are 2-ammonioethanol and 2-trimethylammonioethanol.

The terms "crosslinked" and "crosslinking" in the context of the present disclosure are understood to mean the linking of polymer chains with each other by employing covalent chemical bonding with formation of a network. This covalent linking of polymer chains may take place by employing direct covalent bonding or by employing a molecular fragment bridging the polymer chain. The molecular fragment connects to the polymer chains bridged by the molecular fragment by employing covalent chemical bonding in each case.

The crosslinking of the crosslinked copolymers (b) can be produced using at least one crosslinked monomer. In the process, the crosslinked monomers may be selected from at least one compound of the group of polyunsaturated aromatic monomers (such as divinylbenzene, divinylnaphthalene, trivinylbenzene),polyunsaturated alicyclic monomers (such as1,2,4-trivinylcyclohexane), di-functional esters of phthalic acid (such as diallyl phthalate), polyunsaturated aliphatic monomers (such asdienes, trienes, tetraenes such as isoprene, 1,3-butadiene, 1,5-hexadiene, 1,5,9-decatriene, 1,9-decadiene, 1,5-heptadiene), polyalkenyl ethers (such as triallyl pentaerythritol, diallyl pentaerythritol, diallyl sucrose, octaallyl sucrose, trimethylolpropane diallyl ether), polyunsaturated esters of polyalcohols or polyacids (such as 1,6-hexanediol di(meth)acrylate, tetramethylene tri(meth) acrylate, allyl acrylate, diallyl itaconate, diallyl fumarate, diallyl maleate, diallyl maleate, trimethylolpropane tri (meth)acrylate, trimethylolpropane di(meth)acrylate, polyethylene glycol di(meth)acrylate), alkylene bisacrylamides (such as methylenebisacrylamide, propylene bisacrylamide) hydroxy- and carboxy derivatives of methylene bisacrylamide (such as N,N'-bis-methylol methylene-bis-acrylamide), polyethylene glycol di(meth) acrylates (such as ethylene glycol di(meth)acrylate, diethyleneglycoldi (meth)acrylate, triethylene glycoldi(meth)acrylate), polyunsaturated silanes (such as dimethylvinylsilane, methyltrivinylsilane, allyl dimethylvinylsilane, diallyl dimethylsilane, tetravinylsilane), n-methylolacrylamide; n-alkoxy(meth) acrylamide, wherein the alkoxy group is a (C1 to C18)-alkoxy group, unsaturated hydrolyzable silanes (such as triethoxyvinylsilane, tris-isopropoxy-vinylsilane, 3-triethoxysilyl-propylmethacrylate), hydrolyzable silanes (such as ethyltriethoxysilane, ethyltrimethoxysilane), epoxy-substituted hydrolyzable silanes (such as 2-(3,4-epoxycyclohexypethyltriethoxysilane, 3-glycidoxypropyltrimethyoxysilane) polyisocyanates (such as 1,4-diisocyanatobutane, 1,6-diisocyanatohexane, 1,4-phenylenediamine diisocyanate, 4,4'-oxybis (phenylisocyanate), unsaturated epoxides (such as glycidylmethacrylates, allyl glycidyl ether), polyepoxides (such asdiglycidyl ether, 1,2,5,6-diepoxy hexane, ethylene glycol diglycidyl ether), ethoxylated polyols (such as diols, triols and diphenols, each ethoxylated with from about 2 to about 100 moles of ethylene oxide per mole of hydroxyl groups and terminated with a polymerizable unsaturated group, such as, vinyl ether, allyl ether, acrylate ester, methacrylate ester; examples comprise bisphenol A ethoxylated di(Meth)acrylate, bisphenol F ethoxylated di(meth)acrylate, ethoxylated trimethylolpropane tri(meth)acrylates, acrylate and methacrylate esters of polyols having at least two acrylate ester or methacrylate ester-functionalities (such as trimethylolpropane triacrylate (TMPTA), trimethylolpropane ethoxylated (15) triacrylate (TMPEO15TA), trimethylolpropane dimethacrylate, triethyleneglycoldimethacrylate (TEGDMA), with about 30 mol of ethylene oxide ethoxylated bis-phenol A-dimethacrylate (EOBDMA)).

As contemplated herein, the copolymer (b) can be composed of additional structure units. In one embodiment, the copolymer (b) includes at least about 30 wt. %, such as about 40 to about 98 wt. % and for example at least about 50 to about 95 wt. % of monomers (B-I) and (B-II). However, in an exemplary embodiment of the present disclosure, the copolymer (b) only includes units (B-I) and (B-II) and units to be crosslinked, i.e. it is composed of these structural units.

The at least one unit (B-I) is a (meth)acrylic acid unit and, as contemplated herein, can be a methacrylic acid unit and/or acrylic acid unit. In some embodiments, the unit (B-I) is a methacrylic acid unit (R' in formula (B-I) denotes a methyl group). Corresponding acrylic polymers (b) have been found to be useful for cosmetic applications.

In some embodiments, x in the structural unit (B-II) of the crosslinked acrylate copolymer (b) denotes an integer from about 10 to about 24, such as from about 16 to about 22, for example about 20.

In some embodiments, $R^3$ in unit (B-II) of the crosslinked acrylate copolymer (b) denotes a $(C_{12}$-$C_{20})$-alkyl group, such as a $(C_{14}$-$C_{20})$-alkyl group, also for example a $(C_{16}$-$C_{18})$-alkyl group. The alkyl group in this context may be linear, but can also be branched. $R^3$ denotes, for example, a combination of linear $C_{16}$- and $C_{18}$-alkyl groups, i.e. stearyl- and cetyl groups (INCI: ceteareth). Corresponding acrylic polymers (b) have been found to be useful for cosmetic applications.

In some embodiments, contained crosslinked acrylate copolymer (b) is a crosslinked acrylate copolymer with the INCI designation acrylates-ceteareth-20 methacrylate crosspolymer. In some embodiments, the crosslinked acrylate copolymer (b) is a crosslinked acrylate copolymer available under the trade name BALANCE® RCF (AkzoNobel). The latter is an approximately 30 wt. % dispersion in water.

Additional crosslinked acrylate copolymers (b) are identified by the INCI designation acrylates/steareth-20 methacrylate crosspolymer. In such crosslinked acrylate copolymers, the at least one unit (a1) is a (meth)acrylic acid unit and, as contemplated herein, can be a methacrylic acid unit and/or acrylic acid unit. They have about 20 units of ethylene oxide and are etherified with stearyl alcohol. One such polymer, for example, is available under the trade name Aculyn® 88 (Rohm & Haas). In the commercially available form, this has a solids content of approximately 28 to 33 wt. % and a pH value of from about 3.3 to about 4.3.

Compared to alternative cosmetic agents, the cosmetic preparations as contemplated herein are exemplified by an improved long-term hold, in addition to the aforementioned advantages. A weight ratio of polymers a) and b) in the cosmetic preparations of from about 5:1 to about 1:5, such as from about 3:1 to about 1:3 and for example from about 2:1 to about 1:2 has been found to be useful for the cosmetic properties of the inventive agent.

In one embodiment of the present disclosure, the cosmetic preparation contains the copolymer commercially available under the name Luviquat® Supreme as the copolymer (a) and the copolymer commercially available under the name BALANCE® RCF as the crosslinked acrylate copolymer (b). Particularly good results with regard to a combination of stiffness and long-term hold were achieved with this combination. This polymer combination is useful for styling products in gel form.

Additional properties generally observed by styling products, such as moisture resistance and low stickiness, are also provided with this combination, for example when packaged as hair gel.

The copolymers (a) and (b) may be used in partially neutralized or neutralized form in the cosmetic preparation. At least one alkanolamine may be used for neutralization. The alkanolamines used as an alkalization agent in the context of the present disclosure may be selected from primary amines with a $C_2$-$C_6$-alkyl base body having at least one hydroxyl group. It may be that alkanolamines are selected from the group comprising 2-aminoethan-1-ol (monoethanolamine), 3-(2-hydroxyethyl)-amine (triethanolamine), 3-aminopropan-1-ol, 4-amino-butan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol. As contemplated herein, it is most preferable that alkanolamines are selected from the group of 2-aminoethan-1-ol, 2-amino-2-methylpropan-1-ol and 2-amino-2-methyl-propan-1,3-diol. In this context, 2-amino-2-methylpropanol has been found to be suitable as a neutralization agent. Therefore, some agents as contemplated herein contain 2-amino-2-methylpropanol. The 2-amino-2-methylpropanol may be used in the agents in a quantity which does not exceed the quantity required for neutralization of copolymers (a) and (b). For example, the quantities of 2-amino-2-methylpropanol used in the preparations are from about 80 to about 100%, such as from about 90 to about 100% and for example from about 95 to about 100% of the quantity required for complete neutralization of copolymers (a) and (B). In one embodiment, the proportion by weight of the 2-amino-2-methylpropanol to the total weight of the cosmetic agent is from about 0.05 to about 7.0 wt. %, such as from about 0.1 to about 5.0 wt. % and for example from about 0.1 to about 3.0 wt. %.

In summary, an exemplary cosmetic preparation for temporary deformation of keratinous fibers contains, relative to its total weight:

(a) from about 0.5 to about 8.0 wt. % of at least one copolymer (a) including at least the following monomer used:

(a1) at least one monomer selected from the quaternated N-vinylimidazoles, (a2) at least one monomer selected from the quaternated N-vinyllactams, and (b) from about 0.5 to about 7.0 wt. % of at least one acrylate copolymer (b) differing from the copolymer (a), which includes at least one of the following structural units (B-I) and (B-II):

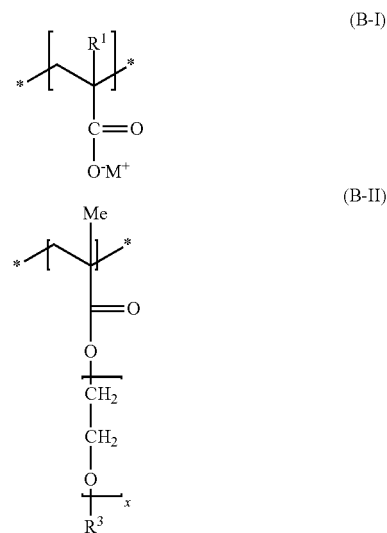

wherein
$R^1$ denotes a methyl group,
$R^3$ denotes a ($C_{14}$-$C_{20}$)-alkyl group,
$M^+$ denotes a physiologically tolerated cation, and
x denotes an integer from about 16 to about 22.

The cosmetic preparation according to the present disclosure may contain one or more additional component(s) which differ(s) from the copolymers (a) and (b) and aid the thickening agent or the gel formation or film formation. Examples are cationic, anionic, nonionic or amphoteric polymers. The proportion by weight of these additional components to the total weight of the cosmetic preparation can be comparatively low due to the present of components (a) and (B) and, for example, be from about 0.02 to about 3 wt. %, such as from about 0.05 to about 1.5 wt. % and for example from about 0.2 to about 0.8 wt. %.

Examples are acrylamide/ammonium acrylate copolymer, acrylamides/dmapa acrylates/methoxy PEG methacrylate copolymer, acrylamidopropyltrimonium chloride/acrylamide copolymer, acrylamidopropyltrimonium chloride/acrylates copolymer, acrylates/acetoacetoxyethyl methacrylate copolymer, acrylates/acrylamide copolymer, acrylates/ammonium methacrylate copolymer, acrylates/t-butylacrylamide copolymer, acrylates/C1-2 succinates/hydroxyacrylates copolymer, acrylates/lauryl acrylate/stearyl acrylate/ethylamine oxide methacrylate copolymer, acrylates/octylacrylamide copolymer, acrylates/octylacrylamide/diphenyl amodimethicone copolymer, acrylates/stearyl acrylate/ethylamine oxide methacrylate copolymer, acrylates/CA copolymer, acrylates/vp copolymer, adipic acid/diethylenetriamine copolymer, adipic acid/dimethylaminohydroxypropyl diethylenetriamine copolymer, adipic acid/epoxypropyl diethylenetriamine copolymer, adipic acid/isophthalic acid/neopentyl glycol/trimethylolpropane copolymer, allyl stearate/VA copolymer, aminoethylacrylate phosphate/acrylates copolymer, aminoethylpropanediol-acrylates/acrylamide copolymer, aminoethylpropanediol-AMPD-acrylates/diacetoneacrylamide copolymer, ammonium va/acrylates copolymer, AMPD-acrylates/diacetoneacrylamide copolymer, AMP-acrylates/allyl methacrylate copolymer, AMP-acrylates/C1-18 alkyl acrylates/C1-8 alkyl acrylamide copolymer, AMP-acrylates/diacetoneacrylamide copolymer, AMP-acrylates/dimethylaminoethylmethacrylate copolymer, bacillus/rice bran extract/soybean extract ferment filtrate, bis-butyloxyamodimethicone/PEG-60 copolymer, butyl acrylate/ethylhexyl methacrylate copolymer, butyl acrylate/hydroxypropyl dimethicone acrylate copolymer, butylated PVP, butyl ester of ethylene/MAcopolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, dimethicone crosspolymer, diphenyl amodimethicone, ethyl ester of PVM/MA copolymer, hydrolyzed wheat protein/PVP crosspolymer, isobutylene/ethylmaleimide/hydroxyethylmaleimide copolymer, isobutylene/MAcopolymer, isobutylmethacrylate/bis-hydroxypropyl dimethicone acrylate copolymer, isopropyl ester of PVM/MA copolymer, lauryl acrylate crosspolymer, lauryl methacrylate/glycol dimethacrylate crosspolymer, MEA-sulfite, methacrylic acid/sodium acrylamidomethyl propane sulfonate copolymer, methacryloyl ethyl betaine/acrylates copolymer, octylacrylamide/acrylates/butylaminoethyl methacrylate copolymer, PEG/PPG-25/25 dimethicone/acrylates copolymer, PEG-8/SMDI copolymer, polyacrylamide, polyacrylate-6, polybeta-alanine/glutaric acid crosspolymer, polybutylene terephthalate, polyester-1, polyethylacrylate, polyethylene terephthalate, polymethacryloyl ethyl betaine, polypentaerythrityl terephthalate, polyperfluoroperhydrophenanthrene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-24, polyquaternium-27, polyquaternium-28, polyquaternium-29, polyquaternium-30, polyquaternium-31, polyquaternium-32, polyquaternium-33, polyquaternium-34, polyquaternium-35, polyquaternium-36, polyquaternium-37, polyquaternium-39, polyquaternium-45, polyquaternium-46, polyquaternium-47, polyquaternium-48, polyquaternium-49, polyquaternium-50, polyquaternium-55, polyquaternium-56, polysilicone-9, polyurethane-1, polyurethane-6, polyurethane-10, polyvinyl acetate, polyvinyl butyral, polyvinylcaprolactam, polyvinylformamide, polyvinyl imidazolinium acetate, polyvinyl methyl ether, potassium butyl ester of pvm/ma copolymer, potassium ethyl ester of PVM/MA copolymer, PPG-70 polyglyceryl-10 ether, PPG-12/SMDI copolymer, ppg-51/SMDIcopolymer, PPG-10 sorbitol, PVM/MA copolymer, PVP, PVPNA/itaconic acid copolymer, PVP/VA/vinyl propionate copolymer, rhizobian gum, rosin acrylate, shellac, sodium butyl ester of PVM/MA copolymer, sodium ethyl ester of PVM/MA copolymer, sodium polyacrylate, sterculia urens gum, terephthalic acid/isophthalic acid/sodium isophthalic acid sulfonate/glycol copolymer, trimethylolpropane triacrylate, trimethylsiloxysilylcarbamoyl pullulan, VA/crotonates copolymer, VA/crotonates/methacryloxybenzophenone-1 copolymer, VA/crotonates/vinyl neodecanoate copolymer, VA/crotonates/vinyl propionate copolymer, VA/DBM copolymer, VA/vinyl butyl benzoate/crotonates copolymer, vinylamine/vinyl alcohol copolymer, vinyl caprolactam/VP/dimethylaminoethyl methacrylate copolymer, VP/acrylates/lauryl methacrylate copolymer, VP/dimethylaminoethylmethacrylate copolymer, VP/DMAPA acrylates copolymer, VP/hexadecene copolymer, VP/VA copolymer, VP/vinyl caprolactam/DMAPA acrylates copolymer, yeast palmitate and styrene/VP copolymer.

The additional component acting as a gel former may be a homopolyacrylic acid (INCI: carbomer), which is commercially available under the name Carbopol® in different embodiments. The carbomer may be contained in a proportion of from about 0.02 to about 3 wt. %, such as from about 0.05 to about 1.5 wt. % and for example from about 0.2 to about 0.8 wt. %, relative to the total weight of the cosmetic preparation.

To further improve the cosmetic effect, some preparations contain, in addition to the copolymers (a) and (b) and an optionally added thickening agent or gel former, a film-forming polymer (c) differing from these ingredient, for example an anionic or nonionic polymer (c).

Examples of nonionic polymers are:
vinylpyrrolidone/vinylester copolymers, which are sold, for example, under the trade name Luviskol (BASF). Luviskol VA 64 and Luviskol VA 73, in each case vinylpyrrolidone/vinylacetate-copolymers, may be nonionic polymers.
cellulose ethers, such as hydroxypropyl cellulose, hydroxyethyl cellulose and methylhydroxypropyl cellulose, are sold, for example, under the trade name Culminaland Benecel (AQUALON).
shellac.
vinylpyrrolidone, which are sold, for example, under the name Luviskol (BASF).
siloxanes. These siloxanes can be water-soluble or non-water-soluble. Fluid and non-fluid siloxanes are suitable, wherein non-fluid siloxanes are to be understood to mean such compounds having a boiling point above about 200° C. under normal pressure. Exemplary siloxanes are polydialkylsiloxanes, such as polydimethylsiloxane, polyalkylarylsiloxanes, such as polyphenylmethylsiloxane, ethoxylated polydialkylsiloxanes and polydialkylsiloxanes which contain amine and/or hydroxyl groups.
glycosidically substituted silicones.

Due to their cosmetic effect in combination with the copolymers a) and b), as contemplated herein, suitably used film-forming polymers are polyvinylpyrrolidones (INCI designation: PVP) and vinylpyrrolidone/vinylacetate copolymers (INCI designation VP/VA copolymer). The proportion by weight of these polymers may be limited to quantities between about 1.0 and about 10 wt. %. Some cosmetic preparations as contemplated herein, therefore, are exemplified in that they contain an additional from about 1.0 to about 10 wt. % of polyvinylpyrrolidone and/or vinylpyrrolidone/vinylacetate-copolymer, such as polyvinylpyrrolidone, relative to their total weight. Exemplary cosmetic agents have a proportion by weight of from about 2.0 to about 8.5 wt. %, such as from about 3.0 to about 7.0 wt. % of polyvinylpyrrolidone and/or vinylpyrrolidone/vinylacetate-copolymers c), relative to the total weight of the cosmetic agent.

The cosmetic preparation can contain additional conventional ingredients of styling products. Additional care substances, in particular, can be mentioned as additional suitable auxiliary substances and additives.

As the nourishing agent, the agent can contain at least one protein hydrolysate and/or a derivate thereof, for example. Protein hydrolysates are product mixtures obtained through the acidically, basically or enzymatically catalyzed decomposition of proteins. As contemplated herein, the expression protein hydrolysates also includes total hydrolysates, as well as individual amino acids and the derivatives thereof, as well as mixtures of various amino acids. The molecular weight of the protein hydrolysates usable as contemplated herein is between about 75, the molecular weight for glycine, and about 200,000, such as from about 75 to about 50,000 and for example from about 75 to about 20,000 Dalton.

The agent as contemplated herein can also contain, as a nourishing agent a vitamin, a provitamin, a vitamin precursor and/or a derivative thereof. As contemplated herein, such vitamins, provitamins and vitamin precursors are usually assigned to the groups A, B, C, E, F and H.

Similar to the addition of glycerine and/or propylene glycol, the addition of panthenol increases the flexibility of the polymer film formed using the inventive agent.

The agent as contemplated herein can also contain, as a nourishing agent, a plant extract, as well as mono- and/or oligosaccharides and/or lipids.

Furthermore, oil bodies are suitable as care substances. The natural and synthetic cosmetic oil bodies include, for example, vegetable oils, liquid paraffin oils, isoparaffin oils and synthetic hydrocarbons, and di-n-alkyl ethers having a total of between about 12 to about 36 carbon atoms, for example between about 12 to about 24 carbon atoms. Cosmetic agents used as contemplated herein contain at least one oil body, such as at least one oil body from the group of silicone oils. The group of silicone oils also includes, for example, dimethicones, which also include cyclomethicones, amino-functional silicones and dimethiconols. Dimethicones can be linear or branched, as well as cyclical or cyclical and branched. Suitable silicone oils or silicone gums are, for example dialkyl- and alkylarylsiloxanes, such as dimethylpolysiloxane and methylphenylpolysiloxane, and alkoxylated, quaternized or anionic derivatives thereof. Cyclical and linear polydialkylsiloxanes, alkoxylated and/or aminated derivatives thereof, dihydroxypolydimethylsiloxanes and polyphenylalkylsiloxanes are exemplary.

Ester oils, i.e. esters of 6-C30 fatty acids with $C_2$-C30 fatty alcohols, for example monoesters of fatty acids with alcohols having from about 2 to about 24 carbon atoms, such as isopropyl myristate (Rilanit® IPM), isononanoic acid C16-18 alkyl esters (Cetiol® SN), 2-ethylhexyl palmitate (Cegesoft® 24), stearic acid-2-ethylhexyl ester (Cetiol® 868), cetyl oleate, glycerol tricaprylate, coconut fatty alcohol caprinate/caprylate (Cetiol® LC), N-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are additional exemplary care oil bodies.

Furthermore, dicarboxylic acid esters, symmetrical, asymmetrical or cyclic esters of carbonic acid with fatty alcohols, trifatty acid esters of saturated and/or unsaturated linear and/or branched fatty acids with glycerol or fatty acid partial glycerides, which are to be understood as monoglycerides, diglycerides and technical mixtures thereof are suitable as care substances.

Furthermore, emulsifiers and/or surfactants may be contained in the inventive preparation. PEG derivatives of hydrated castor oil are exemplary, which are available, for example, under the name PEG Hydrogenated Castor Oil, such as PEG-30 Hydrogenated Castor Oil, PEG-33 Hydrogenated Castor Oil, PEG-35 Hydrogenated Castor Oil, PEG-36 Hydrogenated Castor Oil oder PEG-40 Hydrogenated Castor Oil. As contemplated herein, use of PEG-40 Hydrogenated Castor Oil is exemplary. These are possibly contained in a quantity of from about 0.05 to about 1.5 wt. %, such as from about 0.1 to about 1.0 wt. %, also for example from about 0.2 to about 0.8 wt. % or from about 0.3 to about 0.6 wt. %.

The cosmetic agents contain the ingredients and/or active ingredients in a cosmetically acceptable carrier.

Suitable cosmetically acceptable carriers are aqueous, alcoholic or aqueous-alcoholic media having at least about 10 wt. % water, relative to the total weight of the agent.

It is contemplated that the cosmetic carrier contains water, particularly in a quantity that is at least about 10 wt. %, such as at least about 20.0 wt %. for example at least about 40 wt. % water relative to the total weight of the agent. Exemplary cosmetic agents have a proportion of water between about 50 and about 95 wt. %, such as between about 60 and about 90 wt. % and for example between about 65 and about 85 wt. %, relative to their total weight.

Low alcohols having from about 1 to about 4 carbon atoms conventionally used for cosmetic purpose, such as ethanol and isopropanol, can be used, for example as alcohols.

Examples of water-soluble solvents as a cosolvent are glycerol and/or ethylene glycol and/or 1,2-propylene glycol in a quantity of from about 0 to about 30 wt. % relative to the total agent.

Tabular Overview

A summary of some cosmetic agents is provided in the following tables (specifications in wt. % relative to the total weight of the cosmetic agent, unless otherwise specified).

|  | Formula 1 | Formula 2 | Formula 3 | Formula 4 | Formula 5 |
|---|---|---|---|---|---|
| Copolymer a) | 0.1 to 10 | 0.2 to 9.0 | 0.5 to 8.0 | 0.8 to 7.0 | 1.0 to 7.0 |
| Copolymer b) | 0.1 to 10 | 0.2 to 8.0 | 0.5 to 7.0 | 0.7 to 6.0 | 1.0 to 5.0 |
| Misc | add 100 | add 100 | add 100 | add 100 | add 100 |

|  | Formula 1a | Formula 2a | Formula 3a | Formula 4a | Formula 5a |
|---|---|---|---|---|---|
| POLYQUATERNIUM-68 | 0.1 to 10 | 0.2 to 9.0 | 0.5 to 8.0 | 0.8 to 7.0 | 1.0 to 7.0 |
| Acrylates/Ceteareth-20 Methacrylate Crosspolymer | 0.1 to 10 | 0.2 to 8.0 | 0.5 to 7.0 | 0.7 to 6.0 | 1.0 to 5.0 |
| Misc | add 100 | add 100 | add 100 | add 100 | add 100 |

|  | Formula 1b | Formula 2b | Formula 3b | Formula 4b | Formula 5b |
|---|---|---|---|---|---|
| Luviquat ® Supreme (specifications as solids content) | 0.1 to 10 | 0.2 to 9.0 | 0.5 to 8.0 | 0.8 to 7.0 | 1.0 to 7.0 |

|  | Formula 1b | Formula 2b | Formula 3b | Formula 4b | Formula 5b |
|---|---|---|---|---|---|
| BALANCE ® RCF (specifications as solids content) | 0.1 to 10 | 0.2 to 8.0 | 0.5 to 7.0 | 0.7 to 6.0 | 1.0 to 5.0 |
| Misc | add 100 | add 100 | add 100 | add 100 | add 100 |

|  | Formula 6 | Formula 7 | Formula 8 | Formula 9 | Formula 10 |
|---|---|---|---|---|---|
| Copolymer a) | 0.1 to 10 | 0.2 to 9.0 | 0.5 to 8.0 | 0.8 to 7.0 | 1.0 to 7.0 |
| Copolymer b) | 0.1 to 10 | 0.2 to 8.0 | 0.5 to 7.0 | 0.7 to 6.0 | 1.0 to 5.0 |
| Polyvinylpyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 6a | Formula 7a | Formula 8a | Formula 9a | Formula 10a |
|---|---|---|---|---|---|
| POLYQUATERNIUM-68 | 0.1 to 10 | 0.2 to 9.0 | 0.5 to 8.0 | 0.8 to 7.0 | 1.0 to 7.0 |
| Acrylates/Ceteareth-20 Methacrylate Crosspolymer | 0.1 to 10 | 0.2 to 8.0 | 0.5 to 7.0 | 0.7 to 6.0 | 1.0 to 5.0 |
| Polyvinylpyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 6b | Formula 7b | Formula 8b | Formula 9b | Formula 10b |
|---|---|---|---|---|---|
| Luviquat ® Supreme (specifications as solids content) | 0.1 to 10 | 0.2 to 9.0 | 0.5 to 8.0 | 0.8 to 7.0 | 1.0 to 7.0 |
| BALANCE ® RCF (specifications as solids content) | 0.1 to 10 | 0.2 to 8.0 | 0.5 to 7.0 | 0.7 to 6.0 | 1.0 to 5.0 |
| Polyvinylpyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 11 | Formula 12 | Formula 13 | Formula 14 | Formula 15 |
|---|---|---|---|---|---|
| Copolymer a) | 0.1 to 10 | 0.2 to 9.0 | 0.5 to 8.0 | 0.8 to 7.0 | 1.0 to 7.0 |
| Copolymer b) | 0.1 to 10 | 0.2 to 8.0 | 0.5 to 7.0 | 0.7 to 6.0 | 1.0 to 5.0 |
| Vinylpyrrolidone/Vinylacetate-Copolymer | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 11a | Formula 12a | Formula 13a | Formula 14a | Formula 15a |
|---|---|---|---|---|---|
| POLYQUATERNIUM-68 | 0.1 to 10 | 0.2 to 9.0 | 0.5 to 8.0 | 0.8 to 7.0 | 1.0 to 7.0 |
| Acrylates/Ceteareth-20 Methacrylate Crosspolymer | 0.1 to 10 | 0.2 to 8.0 | 0.5 to 7.0 | 0.7 to 6.0 | 1.0 to 5.0 |
| Vinylpyrrolidone/Vinylacetate-Copolymer | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 1b | Formula 1b | Formula 1b | Formula 1b | Formula 1b |
| --- | --- | --- | --- | --- | --- |
| Luviquat ® Supreme (specifications as solids content) | 0.1 to 10 | 0.2 to 9.0 | 0.5 to 8.0 | 0.8 to 7.0 | 1.0 to 7.0 |
| BALANCE ® RCF (specifications as solids content) | 0.1 to 10 | 0.2 to 8.0 | 0.5 to 7.0 | 0.7 to 6.0 | 1.0 to 5.0 |
| Vinylpyrrolidone/ Vinylacetate-Copolymer | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 16 | Formula 17 | Formula 18 | Formula 19 | Formula 20 |
| --- | --- | --- | --- | --- | --- |
| Copolymer a) | 0.1 to 10 | 0.2 to 9.0 | 0.5 to 8.0 | 0.8 to 7.0 | 1.0 to 7.0 |
| Copolymer b) | 0.1 to 10 | 0.2 to 8.0 | 0.5 to 7.0 | 0.7 to 6.0 | 1.0 to 5.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

|  | Formula 16a | Formula 17a | Formula 18a | Formula 19a | Formula 20a |
| --- | --- | --- | --- | --- | --- |
| POLYQUATERNIUM-68 | 0.1 to 10 | 0.2 to 9.0 | 0.5 to 8.0 | 0.8 to 7.0 | 1.0 to 7.0 |
| Acrylates/Ceteareth-20 Methacrylate Crosspolymer | 0.1 to 10 | 0.2 to 8.0 | 0.5 to 7.0 | 0.7 to 6.0 | 1.0 to 5.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

|  | Formula 16b | Formula 17b | Formula 18b | Formula 19b | Formula 20b |
| --- | --- | --- | --- | --- | --- |
| Luviquat ® Supreme (specifications as solids content) | 0.1 to 10 | 0.2 to 9.0 | 0.5 to 8.0 | 0.8 to 7.0 | 1.0 to 7.0 |
| BALANCE ® RCF (specifications as solids content) | 0.1 to 10 | 0.2 to 8.0 | 0.5 to 7.0 | 0.7 to 6.0 | 1.0 to 5.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

|  | Formula 21 | Formula 22 | Formula 23 | Formula 24 | Formula 25 |
| --- | --- | --- | --- | --- | --- |
| Copolymer a) | 0.1 to 10 | 0.2 to 9.0 | 0.5 to 8.0 | 0.8 to 7.0 | 1.0 to 7.0 |
| Copolymer b) | 0.1 to 10 | 0.2 to 8.0 | 0.5 to 7.0 | 0.7 to 6.0 | 1.0 to 5.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

|  | Formula 21a | Formula 22a | Formula 23a | Formula 24a | Formula 25a |
| --- | --- | --- | --- | --- | --- |
| POLYQUATERNIUM-68 | 0.1 to 10 | 0.2 to 9.0 | 0.5 to 8.0 | 0.8 to 7.0 | 1.0 to 7.0 |
| Acrylates/Ceteareth-20 Methacrylate Crosspolymer | 0.1 to 10 | 0.2 to 8.0 | 0.5 to 7.0 | 0.7 to 6.0 | 1.0 to 5.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

|  | Formula 21b | Formula 22b | Formula 23b | Formula 24b | Formula 25b |
|---|---|---|---|---|---|
| Luviquat ® Supreme (specifications as solids content) | 0.1 to 10 | 0.2 to 9.0 | 0.5 to 8.0 | 0.8 to 7.0 | 1.0 to 7.0 |
| BALANCE ® RCF (specifications as solids content) | 0.1 to 10 | 0.2 to 8.0 | 0.5 to 7.0 | 0.7 to 6.0 | 1.0 to 5.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

|  | Formula 26 | Formula 27 | Formula 28 | Formula 29 | Formula 30 |
|---|---|---|---|---|---|
| Copolymer a) | 0.1 to 10 | 0.2 to 9.0 | 0.5 to 8.0 | 0.8 to 7.0 | 1.0 to 7.0 |
| Copolymer b) | 0.1 to 10 | 0.2 to 8.0 | 0.5 to 7.0 | 0.7 to 6.0 | 1.0 to 5.0 |
| Water | 50 to 95 | 50 to 95 | 60 to 90 | 60 to 90 | 65 to 85 |
| Misc | add 100 | add 100 | add 100 | add 100 | add 100 |

|  | Formula 26a | Formula 27a | Formula 28a | Formula 29a | Formula 30a |
|---|---|---|---|---|---|
| POLYQUATERNIUM-68 | 0.1 to 10 | 0.2 to 9.0 | 0.5 to 8.0 | 0.8 to 7.0 | 1.0 to 7.0 |
| Acrylates/Ceteareth-20 Methacrylate Crosspolymer | 0.1 to 10 | 0.2 to 8.0 | 0.5 to 7.0 | 0.7 to 6.0 | 1.0 to 5.0 |
| Water | 50 to 95 | 50 to 95 | 60 to 90 | 60 to 90 | 65 to 85 |
| Misc | add 100 | add 100 | add 100 | add 100 | add 100 |

|  | Formula 26b | Formula 27b | Formula 28b | Formula 29b | Formula 30b |
|---|---|---|---|---|---|
| Luviquat ® Supreme (specifications as solids content) | 0.1 to 10 | 0.2 to 9.0 | 0.5 to 8.0 | 0.8 to 7.0 | 1.0 to 7.0 |
| BALANCE ® RCF (specifications as solids content) | 0.1 to 10 | 0.2 to 8.0 | 0.5 to 7.0 | 0.7 to 6.0 | 1.0 to 5.0 |
| Water | 0 to 95 | 50 to 95 | 60 to 90 | 60 to 90 | 65 to 85 |
| Misc | add 100 | add 100 | add 100 | add 100 | add 100 |

|  | Formula 31 | Formula 32 | Formula 33 | Formula 34 | Formula 35 |
|---|---|---|---|---|---|
| Copolymer a) | 0.1 to 10 | 0.2 to 9.0 | 0.5 to 8.0 | 0.8 to 7.0 | 1.0 to 7.0 |
| Copolymer b) | 0.1 to 10 | 0.2 to 8.0 | 0.5 to 7.0 | 0.7 to 6.0 | 1.0 to 5.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 31a | Formula 32a | Formula 33a | Formula 34a | Formula 35a |
|---|---|---|---|---|---|
| POLYQUATERNIUM-68 | 0.1 to 10 | 0.2 to 9.0 | 0.5 to 8.0 | 0.8 to 7.0 | 1.0 to 7.0 |
| Acrylates/Ceteareth-20 Methacrylate Crosspolymer | 0.1 to 10 | 0.2 to 8.0 | 0.5 to 7.0 | 0.7 to 6.0 | 1.0 to 5.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 31b | Formula 32b | Formula 33b | Formula 34b | Formula 35b |
|---|---|---|---|---|---|
| Luviquat ® Supreme (specifications as solids content) | 0.1 to 10 | 0.2 to 9.0 | 0.5 to 8.0 | 0.8 to 7.0 | 1.0 to 7.0 |
| BALANCE ® RCF (specifications as solids content) | 0.1 to 10 | 0.2 to 8.0 | 0.5 to 7.0 | 0.7 to 6.0 | 1.0 to 5.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36 | Formula 37 | Formula 38 | Formula 39 | Formula 40 |
|---|---|---|---|---|---|
| Copolymer a) | 0.1 to 10 | 0.2 to 9.0 | 0.5 to 8.0 | 0.8 to 7.0 | 1.0 to 7.0 |
| Copolymer b) | 0.1 to 10 | 0.2 to 8.0 | 0.5 to 7.0 | 0.7 to 6.0 | 1.0 to 5.0 |
| Vinylpyrrolidone/ Vinylacetate-Copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36a | Formula 37a | Formula 38a | Formula 39a | Formula 40a |
|---|---|---|---|---|---|
| POLYQUATERNIUM-68 | 0.1 to 10 | 0.2 to 9.0 | 0.5 to 8.0 | 0.8 to 7.0 | 1.0 to 7.0 |
| Acrylates/Ceteareth-20 Methacrylate Crosspolymer | 0.1 to 10 | 0.2 to 8.0 | 0.5 to 7.0 | 0.7 to 6.0 | 1.0 to 5.0 |
| Vinylpyrrolidone/ Vinylacetate-Copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36b | Formula 37b | Formula 38b | Formula 39b | Formula 40b |
|---|---|---|---|---|---|
| Luviquat ® Supreme (specifications as solids content) | 0.1 to 10 | 0.2 to 9.0 | 0.5 to 8.0 | 0.8 to 7.0 | 1.0 to 7.0 |
| BALANCE ® RCF (specifications as solids content) | 0.1 to 10 | 0.2 to 8.0 | 0.5 to 7.0 | 0.7 to 6.0 | 1.0 to 5.0 |
| Vinylpyrrolidone/ Vinylacetate-Copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 41 | Formula 42 | Formula 43 | Formula 44 | Formula 45 |
|---|---|---|---|---|---|
| Copolymer a) | 0.1 to 10 | 0.2 to 9.0 | 0.5 to 8.0 | 0.8 to 7.0 | 1.0 to 7.0 |
| Copolymer b) | 0.1 to 10 | 0.2 to 8.0 | 0.5 to 7.0 | 0.7 to 6.0 | 1.0 to 5.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 41a | Formula 42a | Formula 43a | Formula 44a | Formula 45a |
|---|---|---|---|---|---|
| POLYQUATERNIUM-68 | 0.1 to 10 | 0.2 to 9.0 | 0.5 to 8.0 | 0.8 to 7.0 | 1.0 to 7.0 |

-continued

|  | Formula 41a | Formula 42a | Formula 43a | Formula 44a | Formula 45a |
|---|---|---|---|---|---|
| Acrylates/Ceteareth-20 Methacrylate Crosspolymer | 0.1 to 10 | 0.2 to 8.0 | 0.5 to 7.0 | 0.7 to 6.0 | 1.0 to 5.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 41b | Formula 42b | Formula 43b | Formula 44b | Formula 45b |
|---|---|---|---|---|---|
| Luviquat ® Supreme (specifications as solids content) | 0.1 to 10 | 0.2 to 9.0 | 0.5 to 8.0 | 0.8 to 7.0 | 1.0 to 7.0 |
| BALANCE ® RCF (specifications as solids content) | 0.1 to 10 | 0.2 to 8.0 | 0.5 to 7.0 | 0.7 to 6.0 | 1.0 to 5.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 46 | Formula 47 | Formula 48 | Formula 49 | Formula 50 |
|---|---|---|---|---|---|
| Copolymer a) | 0.1 to 10 | 0.2 to 9.0 | 0.5 to 8.0 | 0.8 to 7.0 | 1.0 to 7.0 |
| Copolymer b) | 0.1 to 10 | 0.2 to 8.0 | 0.5 to 7.0 | 0.7 to 6.0 | 1.0 to 5.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

|  | Formula 46a | Formula 47a | Formula 48a | Formula 49a | Formula 50a |
|---|---|---|---|---|---|
| POLYQUATERNIUM-68 | 0.1 to 10 | 0.2 to 9.0 | 0.5 to 8.0 | 0.8 to 7.0 | 1.0 to 7.0 |
| Acrylates/Ceteareth-20 Methacrylate Crosspolymer | 0.1 to 10 | 0.2 to 8.0 | 0.5 to 7.0 | 0.7 to 6.0 | 1.0 to 5.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

|  | Formula 46b | Formula 47b | Formula 48b | Formula 49b | Formula 50b |
|---|---|---|---|---|---|
| Luviquat ® Supreme (specifications as solids content) | 0.1 to 10 | 0.2 to 9.0 | 0.5 to 8.0 | 0.8 to 7.0 | 1.0 to 7.0 |
| BALANCE ® RCF (specifications as solids content) | 0.1 to 10 | 0.2 to 8.0 | 0.5 to 7.0 | 0.7 to 6.0 | 1.0 to 5.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

In the context of the present disclosure, "Misc" is understood to mean a cosmetic carrier, for example water (unless indicated separately) and optionally additional conventional components of styling products.

The cosmetic preparation of the present disclosure can be packed in the conventional forms for temporary deformation of hair, such as hair gel, hairspray, mousse or hair wax. Packaging as hair gel is an example.

Hair mousse and hairsprays may utilize the presence of propellants. As contemplated herein, however, these propellants might not contain any or only minor quantities of hydrocarbons. Propane, propane/butane mixtures and dimethyl ether are particularly suitable propellants as contemplated herein.

The present disclosure also relates to the use of cosmetic preparations for temporary deformation of keratinous fibers, such as of human hair, as well as a method for temporary deformation of keratinous fibers, such as human hair, wherein the cosmetic preparation is applied on keratinous fibers.

An additional subject of this patent application is the use of acosmetic preparation for improvement of the hold of temporarily deformed keratinous fibers.

Another subject of this patent application is the use of a cosmetic preparation for improvement of the moisture resistance of temporarily deformed keratinous fibers.

EXAMPLES

The following hair gels were produced:

| Component/ raw material | INCI designation or chemical name | V1 | V2 | E1 |
|---|---|---|---|---|
| Luviquat ® Supreme (specifications as solids content)1 | POLYQUATERNIUM-68 | 5.0 | — | 2.5 |
| BALANCE ® RCF[2] | Acrylates/Ceteareth-20 Methacrylate Crosspolymer | — | 3.3 | 1.65 |
| AMP-ULTRA PC 2000 | Aminomethyl Propanol | — | 0.3 | 0.15 |
| Water | | 95.0 | 96.4 | 95.7 |
| Total | | 100 | 100 | 100 |

[1] 20 wt. % of active substance in water
[2] 30 wt. % of active substance in water The quantity specifications in the table specified as wt. % of the respective raw material, relative to the total preparation. The polymer content in each of the preparations V1, V2 and E1 was about 1.0 wt. %.

The maximum hold (N) was determined for the produced styling agents by employing a 3PB test (3-point bending test) on cleaned Kerling hair strands (mean value of 5 hair strands each):

| | V1 | V2 | E1 |
|---|---|---|---|
| Fmax | 2.8 | 2.4 | 3.8 |

The inventive polymer combination E1 demonstrated a clear overadditive, synergistic effect with regard to the maximum hold.

For the produced styling agent, the moisture resistance on cleaned Kerling hair strands was determined by employing an HHCR test (High Humidity Curl Retention test: 6 h) (average of about 5 hair strands each):

| | V1 | V2 | E1 |
|---|---|---|---|
| HHCR | 77% | 73% | 88% |

The inventive polymer combination E1 demonstrated a clear overadditive, synergistic effect with regard to the moisture resistance.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:
1. A cosmetic preparation for temporary deformation of keratinous fibers, which comprises:
 a) from about 1 to about 7 wt % of polyquaternium-68
 b) from about 1 to about 5 wt % of acrylates/cetereath-20 methacrylate crosspolymer
 c) aminomethyl propanol
 d) from about 50 to about 95% water
 wherein the copolymer (a) is present in the cosmetic composition in an amount from 0.1% to 10% and the copolymer (b) is present in the cosmetic composition in an amount from 0.1% to 10%, both by weight of the overall cosmetic composition, and
 (c) water.
2. Method for temporary deformation of keratinous fibers, where the cosmetic preparation according to claim 1 is applied on keratinous fibers.

* * * * *